US005540710A

United States Patent [19]

Yoo

[11] Patent Number: 5,540,710

[45] Date of Patent: Jul. 30, 1996

[54] NEEDLE FOR HANDS

[76] Inventor: Tae W. Yoo, 807, 1-Dong, Hanyang, Apt. 32-5, Banpo-dong, Seocho-ku, Seoul, Rep. of Korea

[21] Appl. No.: 312,466

[22] Filed: Sep. 26, 1994

[30] Foreign Application Priority Data

Jul. 8, 1994 [KR] Rep. of Korea ...................... 94-16851

[51] Int. Cl.[6] ...................................................... A61B 17/34

[52] U.S. Cl. ............................................ 606/189; 128/907

[58] Field of Search .................................... 606/185, 186, 606/187, 188, 189, 129; 128/907; 30/366, 340, 341, 342, 343, 344; 16/110 R

[56] References Cited

U.S. PATENT DOCUMENTS 5,123,315 4/1992 Asbery ...................................... 30/366
5,201,751 4/1993 Cohen ..................................... 606/189

FOREIGN PATENT DOCUMENTS 1187759 5/1985 Canada .................................. 606/189
197712 12/1977 U.S.S.R. ................................ 606/189
1782167 12/1992 U.S.S.R. ................................ 606/189

*Primary Examiner*—Tamara L. Graysay
*Attorney, Agent, or Firm*—Richard M. Goldberg

[57] ABSTRACT

A needle assembly for performing acupuncture treatment, includes a needle holder formed from a tubular member, the needle holder having a tubular shaft portion formed from an upper portion of the tubular member, a pressed portion integrally formed at a lower end of the tubular shaft portion and formed from a flattened lower portion of the tubular member, and a needle held within the needle holder and projecting from a lower end of the pressed portion. Thus, by directly pricking needle points after holding the pressed portion and the shaft portion with a hand without a inserter, it is convenient to apply acupuncture and to control the pricking depth. Furthermore, by rotating the protruded portion from side to side, it is easy to stimulate needle points, so that the effect of the acupuncture treatment can be enhanced.

8 Claims, 4 Drawing Sheets

NEEDLE FOR HANDS

BACKGROUND OF THE INVENTION

1. Field of the Invention

The present invention relates to a needle for hands which comprises a protruded portion and a pressed portion. More particularly, it relates to an invention which is convenient for use and can enhance the effect of the acupuncture.

2. Description of the Prior Art

Conventional inventions of this type of needle, as shown in FIGS. 4(*a*), (*b*), comprise a rod (21) which was coiled from the top of a needle (20) to a fixed part, having a diameter of within 0.2 mm and a length of about 15 mm. The needle is so small that acupuncture cannot directly be applied by hand. Thus, when the acupuncture is applied, an inserter, as shown in FIGS. 5(*a*), (*b*), must be used.

According to the conventional invention, the needle is raised by a magnet (32) fixed to a plunger (31), and inserted into the inserter (30), and then it is laid on a needle point to apply acupuncture to the front or back of the hand. Then, when the lift plunger (31) is released, the needle pricks the skin by the force of gravity of the plunger (31).

As mentioned above, according to said invention, it is necessary to use several steps in applying acupuncture. Therefore, when there are many needle points to be applied with acupuncture, it is inconvenient for use. Furthermore, owing to the constant force of gravity of the plunger, there may be differences in the in inserting depth according to the individual characteristic of the skin or the difference of the skin of the front and back of the hand. Thus, there are problems that a deep prick will cause pain to a user in the case of thin skin, and a slight prick will be inefficient for the acupuncture treatment in the case of thick skin.

SUMMARY OF THE INVENTION

In the light of the foregoing, the present invention has an object to provide a needle for hands which is convenient in applying acupuncture without the inserter, and which is easy in stimulating needle points.

To attain the objects described above according to this invention, a needle assembly for performing acupuncture treatment, includes a needle holder formed from a tubular member, the needle holder having a tubular shaft portion formed from an upper portion of the tubular member, a pressed portion integrally formed at a lower end of the tubular shaft portion and formed from a flattened lower portion of the tubular member, and a needle held within the needle holder and projecting from a lower end of the pressed portion.

BRIEF DESCRIPTION OF THE DRAWINGS

The other objects and features of the present invention will be hereinafter explained in detail with reference to the accompanying drawings, wherein.

DESCRIPTION OF THE PREFERRED EMBODIMENT

After inserting a shaft portion(14) into a round tube, a round tube portion of the round tube, having a length of about 5–8 mm from the top, is unpressed, and is appointed as a protruded portion (12). Below the protruded portion (12), a pressed portion (11) is formed by pressing the round tube flat to fix the shaft portion (14), the pressed portion (11) having a length of about 6–8 mm and a width of about 4–6 mm. Then, a needle portion (13) is projected from the end of the pressed portion (11) with length of about 1–3 min. In general, the pricking depth is about 1–2 mm.

It is to be understood that although the present invention has been described in detail with respect to a preferred embodiment thereof various other embodiments and variants are possible which embodiments and variants are intended to be covered by the following claims.

Figure 1:
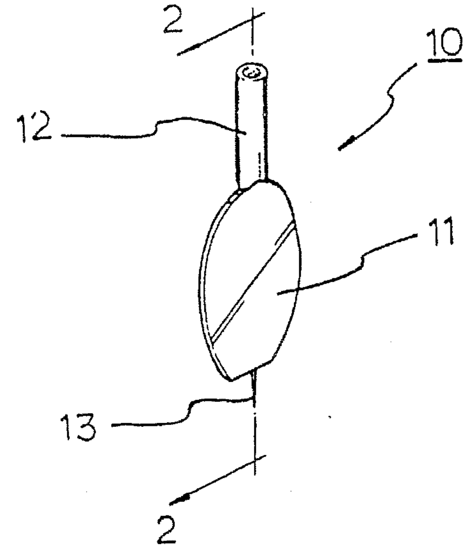
FIG. 1 is a perspective view showing the present invention.
Figure 2:
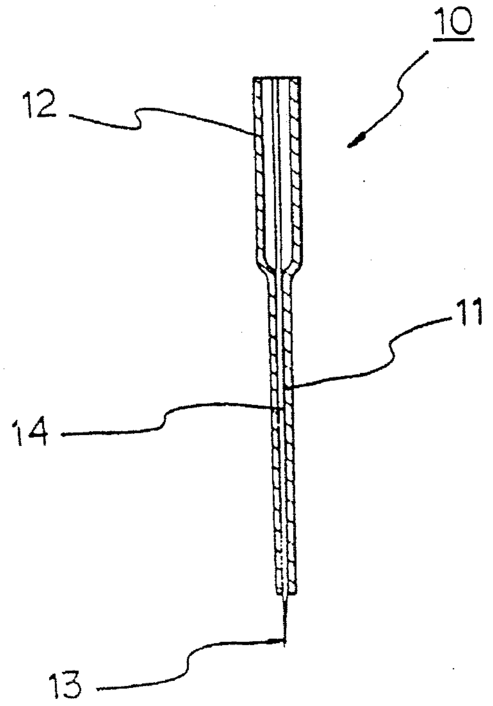
FIG. 2 is an enlarged cross-sectional view taken along line 2—2 of FIG. 1.
Figure 3A:
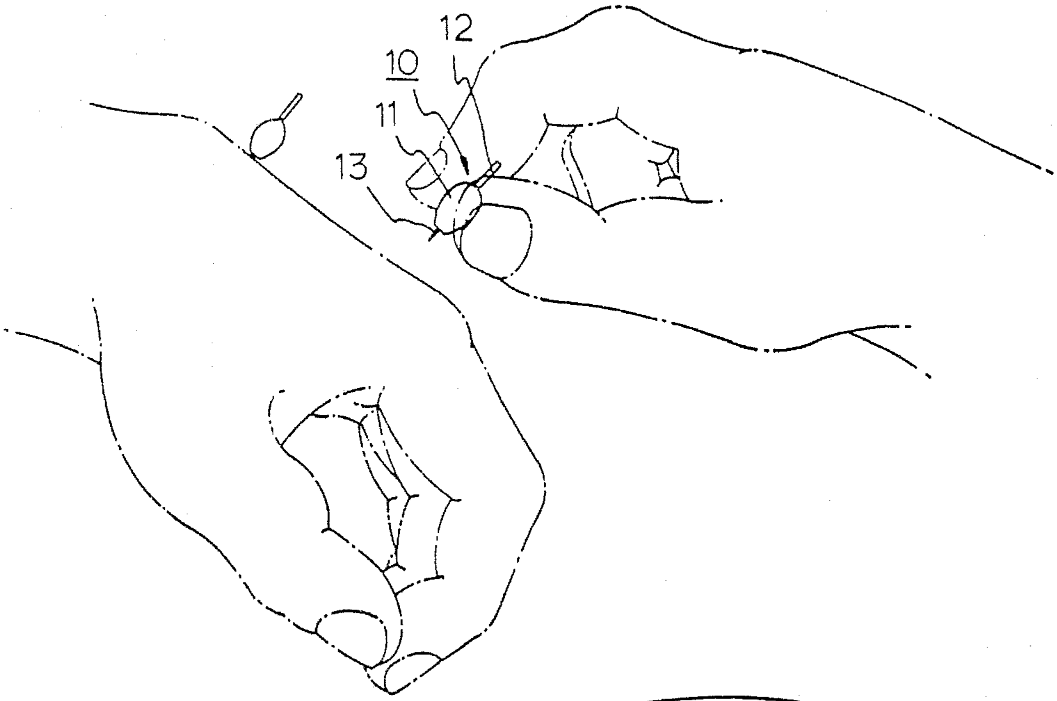
FIGS. 3(*a*) and 3(*b*) are perspective views showing the use thereof.
Figure 3B:
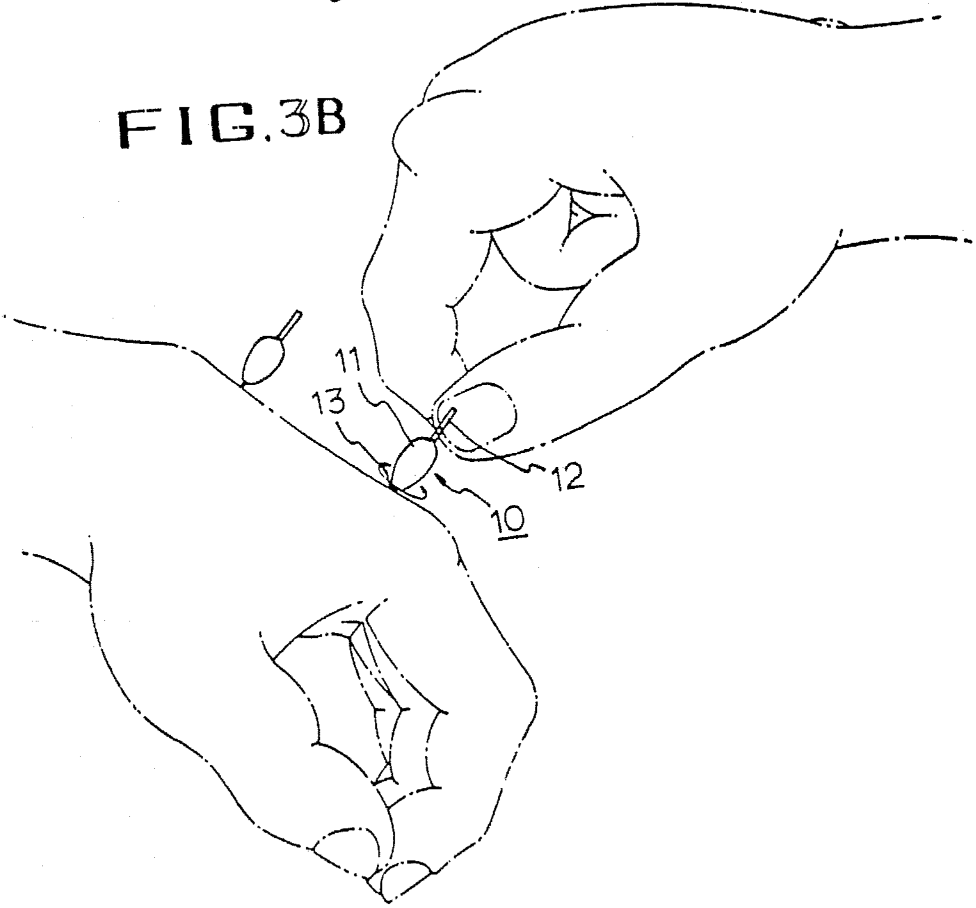
Figure 4A:
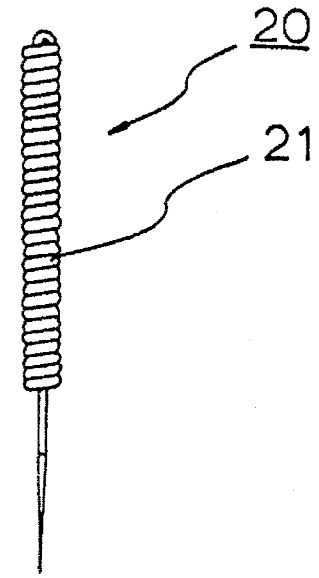
FIG.4A PRIOR ART
FIGS. 4(*a*) and 4(*b*), are a front elevational view and a cross-sectional view showing the conventional invention.
Figure 4B:
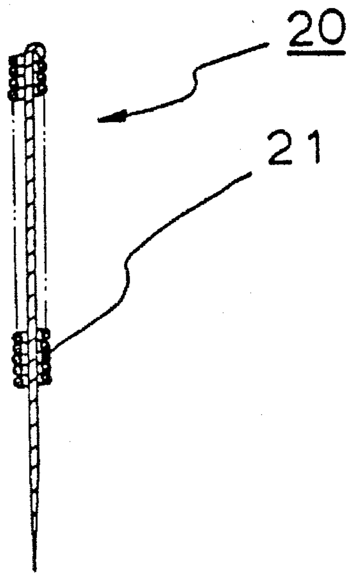
FIG.4B PRIOR ART
Figure 5A:
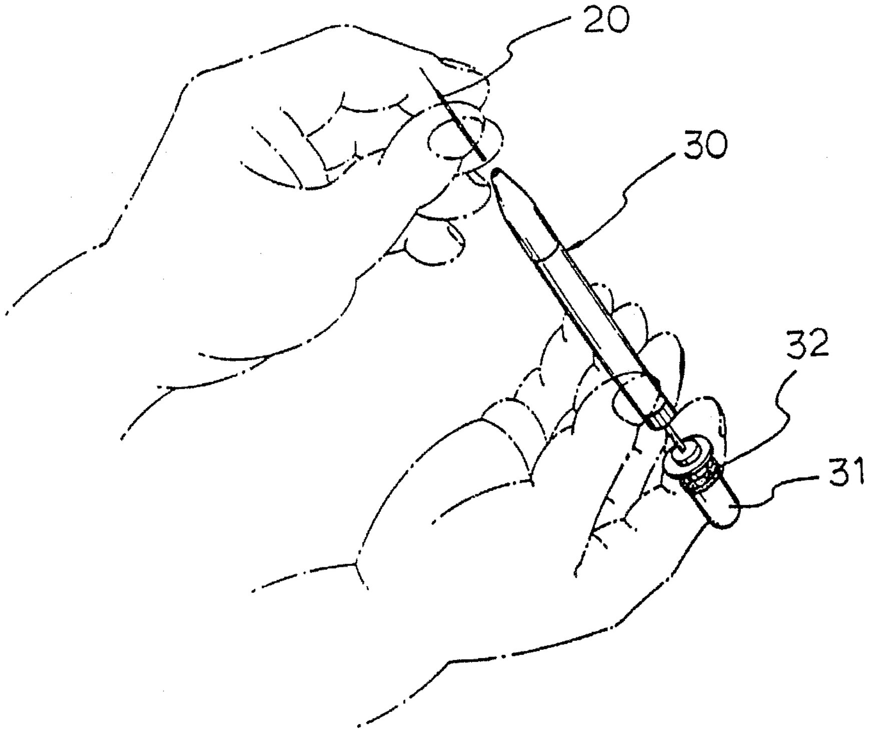
FIG. 5A PRIOR ART
FIGS. 5(*a*) and 5(*b*) are perspective views showing the use of the conventional invention.
Figure 5B:
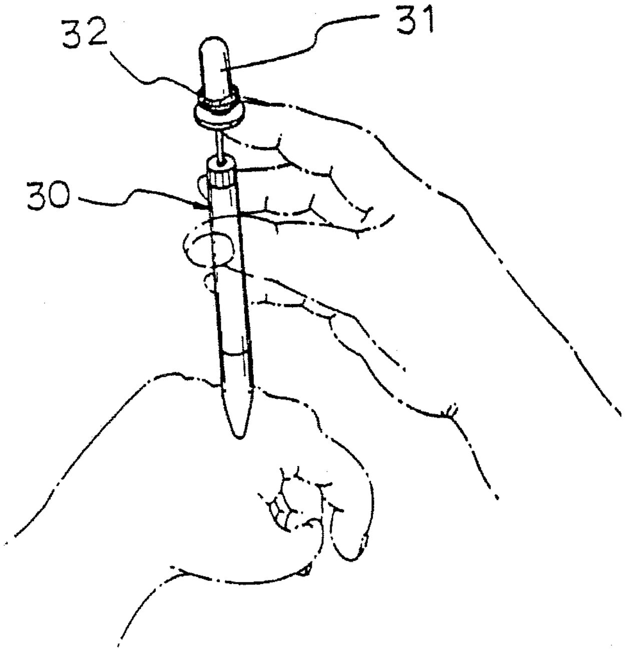
FIG. 5B PRIOR ART

As shown the FIGS. 3(*a*) and 3(*b*), by forming the pressed portion (11) at the shaft portion (14), a user can easily hold the pressed portion (11) and the protruded portion (12), and directly prick the skin with a hand without the inserter. Therefore, the present invention can overcome the inconvenience according to the use of the inserter, and can easily control the pricking depth. Furthermore, by rotating the protruded portion (12) while pricking the skin with the needle portion (13), the needle points can easily be stimulated and the effect of the acupuncture treatment can be enhanced.

What is claimed is:

1. A needle assembly for performing acupuncture treatment, comprising:

a rigid needle having a diameter;

a needle holder formed from a tubular member, said needle holder including:

a tubular shaft portion formed from an upper portion of said tubular member, said tubular shaft portion having an inner diameter greater than the diameter of said needle; and a pressed portion integrally formed at a lower end of said tubular shaft portion and formed from a flattened lower portion of said tubular member, said pressed portion having an inner diameter less than the diameter of said tubular shaft portion and which clamps said needle therein to prevent movement thereof; and said needle projecting from a lower end of said pressed portion by a fixed distance.

2. A needle assembly according to claim 1, wherein said pressed portion has a generally circular configuration in an elevation view.

3. A needle assembly according to claim 1, wherein said tubular shaft portion has a length ranging from about 5 to 8 mm.

4. A needle assembly according to claim 1, wherein said pressed portion has a length ranging from about 6 to 8 mm.

5. A needle assembly according to claim 4, wherein said pressed portion has a width ranging from about 4 to 6 mm.

6. A needle assembly according to claim 1, wherein said fixed distance is a length ranging from about 1 to 3 mm.

7. A needle assembly according to claim 1, wherein said needle extends through said tubular shaft portion and said pressed portion.

8. A needle assembly according to claim 1, wherein said tubular shaft portion has an outer diameter and said pressed portion has a thickness less than the outer diameter of said tubular shaft portion.

* * * * *